(12) United States Patent
Jeong et al.

(10) Patent No.: US 11,788,746 B2
(45) Date of Patent: Oct. 17, 2023

(54) FLUID TREATMENT DEVICE

(71) Applicant: SEOUL VIOSYS CO., LTD., Gyeonggi-do (KR)

(72) Inventors: Jae Hak Jeong, Gyeonggi-do (KR); Ji Won Kim, Gyeonggi-do (KR); Sang Chul Shin, Gyeonggi-do (KR); Woong Ki Jeong, Gyeonggi-do (KR)

(73) Assignee: SEOUL VIOSYS CO., LTD., Ansan-si (KR)

(*) Notice: Subject to any disclaimer, the term of this patent is extended or adjusted under 35 U.S.C. 154(b) by 0 days.

(21) Appl. No.: 16/938,562

(22) Filed: Jul. 24, 2020

(65) Prior Publication Data
US 2020/0355378 A1 Nov. 12, 2020

Related U.S. Application Data

(63) Continuation of application No. PCT/KR2019/001063, filed on Jan. 25, 2019.

(30) Foreign Application Priority Data

Jan. 26, 2018 (KR) .................. 10-2018-0009795

(51) Int. Cl.
*F24F 8/167* (2021.01)
*A61L 9/20* (2006.01)
(Continued)

(52) U.S. Cl.
CPC .............. *F24F 8/167* (2021.01); *A61L 9/205* (2013.01); *F24F 8/10* (2021.01); *F24F 8/24* (2021.01);
(Continued)

(58) Field of Classification Search
None
See application file for complete search history.

(56) References Cited

U.S. PATENT DOCUMENTS

2006/0086252 A1* 4/2006 Huang ................. B01D 53/885
96/134
2010/0135864 A1* 6/2010 Taniguchi ................. A61L 9/18
502/77
(Continued)

FOREIGN PATENT DOCUMENTS

CN 205664497 U 10/2016
EP 2937139 A1 10/2015
(Continued)

OTHER PUBLICATIONS

Document entitled WO2011135686A1 Photocatalyst Filter Unit and Air Purifying Device, machine translation of WO2011135686A1 provided by Espacenet (Year: 2011).*
(Continued)

*Primary Examiner* — Holly Kipouros
(74) *Attorney, Agent, or Firm* — Perkins Coie LLP

(57) ABSTRACT

A fluid treatment device includes a photocatalytic filter for deodorizing and sterilizing a fluid; a frame for fixing the photocatalytic filter; and a light source unit coupled to the frame. The light source unit includes a light source support member and a light emitting diode, which is provided on the light source support member so as to emit light at the photocatalytic filter. The frame and the light source support member are coupled in a form that separates the photocatalytic filter from the light emitting diode.

20 Claims, 14 Drawing Sheets

(51) Int. Cl.
*F24F 8/10* (2021.01)
*F24F 8/24* (2021.01)
(52) U.S. Cl.
CPC ....... *A61L 2209/12* (2013.01); *A61L 2209/14* (2013.01); *A61L 2209/15* (2013.01); *A61L 2209/16* (2013.01)

(56) References Cited

U.S. PATENT DOCUMENTS

| | | |
|---|---|---|
| 2013/0034470 A1 | 2/2013 | Wang et al. |
| 2013/0052090 A1 | 2/2013 | Bohlen |
| 2014/0030144 A1* | 1/2014 | Krosney ............... B01D 53/007 422/4 |
| 2015/0044101 A1* | 2/2015 | Koo ......................... F24F 8/192 422/121 |
| 2016/0008804 A1* | 1/2016 | Balikhin .................. B01J 35/10 502/350 |
| 2018/0104374 A1* | 4/2018 | Kim .................... B01D 53/0454 |
| 2018/0110890 A1* | 4/2018 | Matsui ....................... A61L 2/10 |
| 2018/0207311 A1* | 7/2018 | Cho ......................... A61L 9/205 |
| 2018/0280559 A1* | 10/2018 | Sambandan ............. B01J 23/30 |
| 2018/0344890 A1* | 12/2018 | Watanabe ............... F24F 13/28 |
| 2019/0083674 A1* | 3/2019 | Jeong ..................... A61L 9/205 |

FOREIGN PATENT DOCUMENTS

| | | | |
|---|---|---|---|
| JP | 08-103631 A | 4/1996 | |
| JP | 2600103 A | 4/1996 | |
| JP | 2000325445 A | 11/2000 | |
| JP | 2000325724 A | 11/2000 | |
| JP | 2003203746 A | 7/2003 | |
| JP | 2006501020 A | 1/2006 | |
| JP | 2006280428 A | 10/2006 | |
| JP | 2008114131 A | 5/2008 | |
| JP | 2008264713 A | 11/2008 | |
| JP | 2015062640 A | 4/2015 | |
| JP | 2015070959 A | 4/2015 | |
| JP | 3207938 U | 12/2016 | |
| JP | 2017536884 A | 12/2017 | |
| JP | 2017537294 A | 12/2017 | |
| KR | 10-2003-0009685 | 2/2003 | |
| KR | 20080100047 A | 11/2008 | |
| KR | 20090011272 * | 11/2009 | |
| KR | 20100022893 A | 3/2010 | |
| KR | 10-2010-0087074 | 8/2010 | |
| KR | 20120047174 * | 5/2012 | |
| KR | 10-2013-0125436 | 11/2013 | |
| KR | 10-2015-0071255 | 6/2015 | |
| KR | 10-2015-0087496 | 7/2015 | |
| KR | 20160068075 A * | 6/2016 | ........... F25D 17/042 |
| KR | 20160098685 * | 8/2016 | |
| KR | 1020160132764 A | 11/2016 | |
| KR | 20170008503 A | 1/2017 | |
| KR | 20170026966 A | 3/2017 | |
| RU | 2262455 C1 | 10/2005 | |
| RU | 48815 U1 | 11/2005 | |
| RU | 2647839 C2 | 3/2018 | |
| WO | 2011135686 A1 | 11/2011 | |
| WO | WO-2011135686 A1 * | 11/2011 | ............ B01J 35/004 |
| WO | 2011162059 A1 | 12/2011 | |
| WO | 2013047710 A1 | 4/2013 | |
| WO | 2016089088 A1 | 6/2016 | |
| WO | 2016093677 A1 | 6/2016 | |
| WO | 2017034188 A1 | 3/2017 | |

OTHER PUBLICATIONS

Document entitled KR20160098685A Space Sterilization Method With Multiple Wavelength Ultraviolet Lights and Space Sterilization Module Using the Method Thereof, machine translation of KR20160098685A provided by EPO, original document published 2016 (Year: 2016).*
Document entitled KR20120047174A Air Cleaner With Ultraviolet Light Emitting Diode, machine translation of KR20120047174A provided by EPO, original document published 2012 (Year: 2012).*
Document entitled Air Cleaner, machine translation of KR20090011272U provided by Clarivate, original document published 2009 (Year: 2009).*
International Search Report for International Application PCT/KR2019/001063, dated May 10, 2019.
Supplementary European Search Report for European Application No. 19743312.1, dated Oct. 14, 2021, 10 pages.
Examination Report issued to corresponding IN Application No. 202037036243, dated May 11, 2022, 5 pages.
Office Action from corresponding Korean Patent Application No. 10-2018-0009795, dated Oct. 7, 2022 (8 pages).
Office Action from corresponding Japanese Patent Application No. 2020-540705, dated Sep. 27, 2022 (12 pages).
Supplementary Russian Search Report for Russian Application No. 2022105764, dated Aug. 23, 2022, 2 pages.
Office Action issued in Corresponding Russian Application No. 2022105764, dated Aug. 26, 2022, 5 pages.
English Translation of Office Action from corresponding Japanese Patent Application No. 2020-540705, dated Apr. 4, 2023 (13 pages).
English translation of Japanese Office Action from corresponding Japanese Patent Application No. 2020540705 dated Aug. 22, 2023 (8 pages).

* cited by examiner

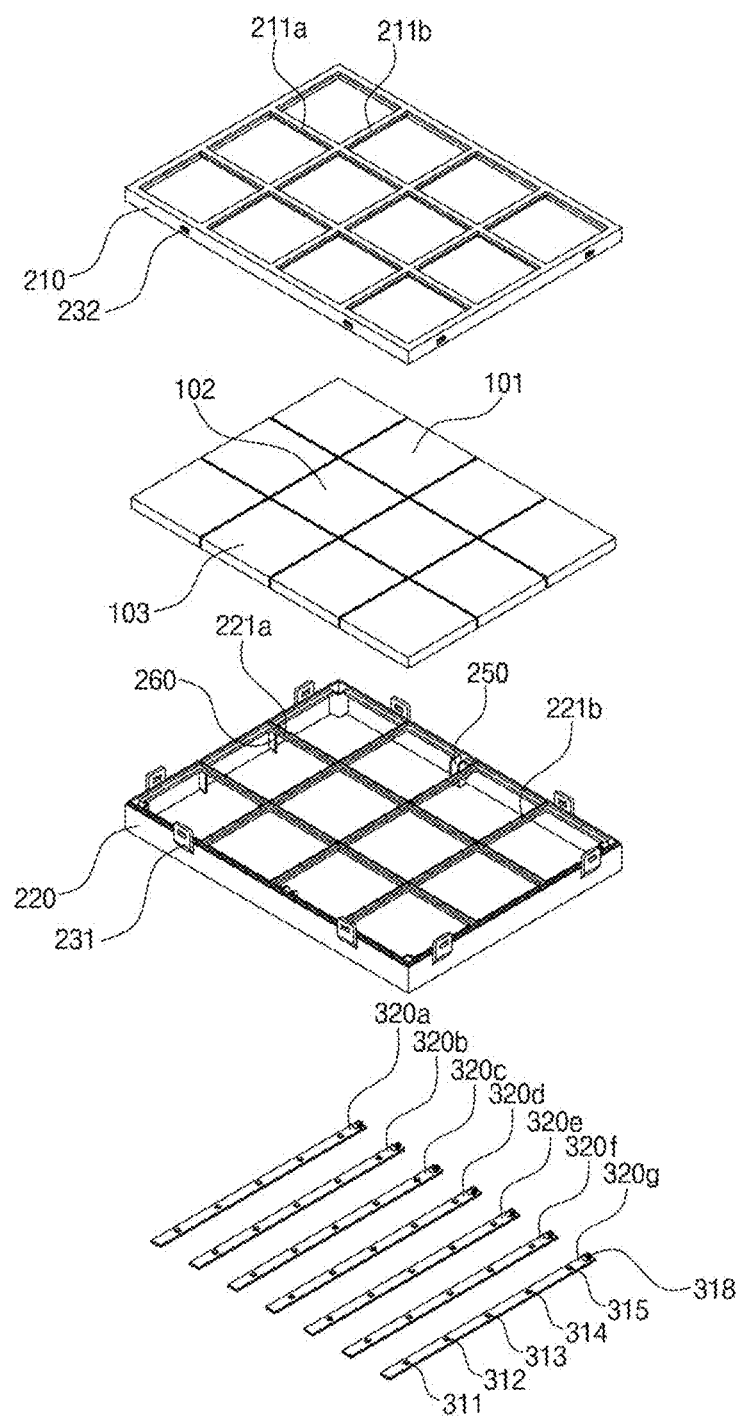

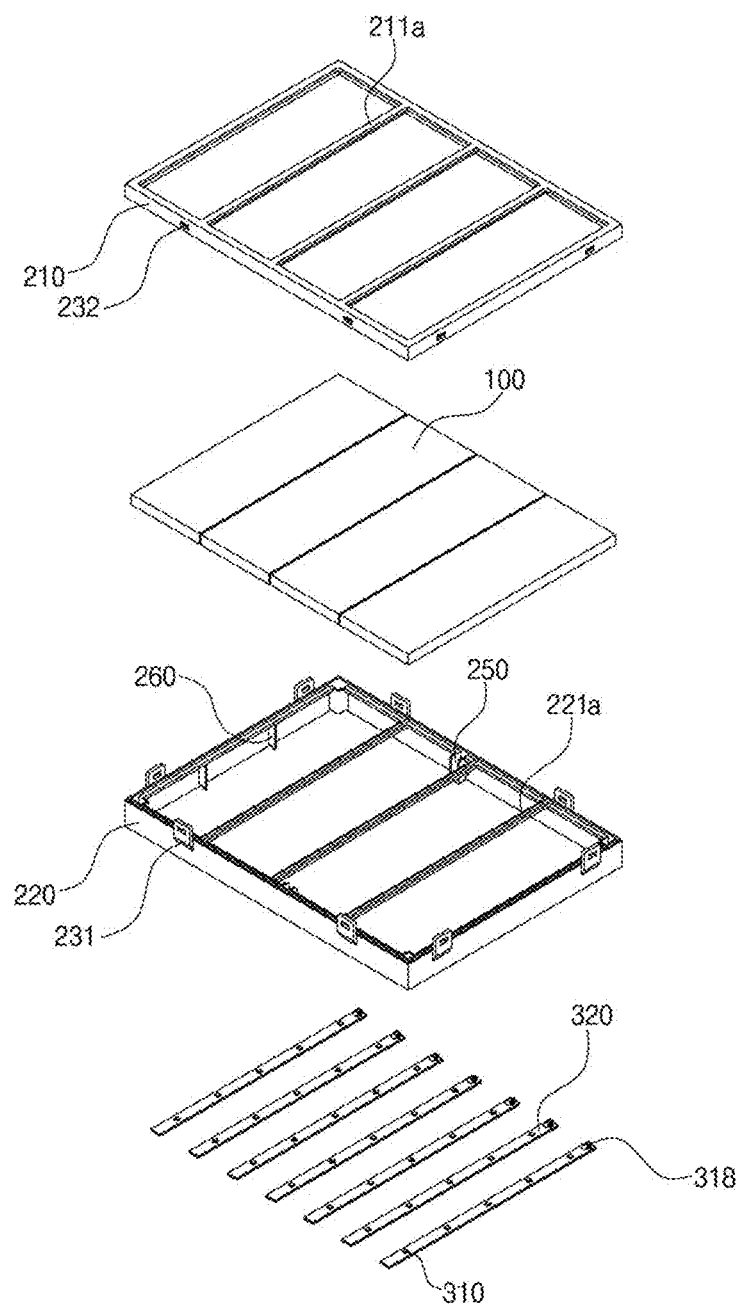

Acetaldehyde

FLUID TREATMENT DEVICE

CROSS-REFERENCE TO RELATED APPLICATIONS AND PRIORITY

This application is a continuation of PCT/KR2019/001063 filed on Jan. 25, 2019, which claims the benefit of Korean Patent Application No. 10-2018-0009765, filed on Jan. 26, 2018, in the Korean Intellectual Property Office, the disclosures of which are incorporated herein in their entireties by reference.

TECHNICAL FIELD

Embodiments of the present invention relate to a fluid treatment device and, more particularly, to a fluid treatment device used in air conditioners.

BACKGROUND

An air conditioner is an apparatus for circulating indoor air. Air conditioners can provide air conditioning in an indoor space by heating or cooling air in the space. Besides air conditioning, air conditioners can provide purification of indoor air. That is, air conditioners can be used to remove indoor air pollutants, such as fine dust, chemicals from wallpaper or flooring, and cigarette smoke.

However, typical air conditioners are only capable of filtering air pollutants using a filter. Thus, in typical air conditioners, air pollutants still remain in a filter without being completely removed. This type of air purification has obvious limitations. One example is that such a typical air conditioner, which does not remove air pollutants at the source, may not work properly if a filter at the end of its life is not replaced. In addition, air pollutants remaining in the air conditioner are likely to spread back into the air during work such as a filter replacement. Accordingly, there is a need for an air conditioner capable of removing air pollutants at the source.

Furthermore, high-rise buildings and large-size indoor shopping malls have increased the demand for large-scale air conditioners. Therefore, there is also a need for a large-scale air conditioner suitable for use in large-size buildings.

SUMMARY

Embodiments of the present invention provide a fluid treatment device that can remove air pollutants at the source.

Embodiments of the present invention provide a fluid treatment device that can be used in large air conditioners.

In accordance with embodiments of the present invention, a fluid treatment device includes: a photocatalytic filter deodorizing and sterilizing a fluid; a frame holding the photocatalytic filter; and a light source unit coupled to the frame, the light source unit including: a light source support member; and a light emitting diode disposed on the light source support member to emit light toward the photocatalytic filter, wherein the frame is coupled to the light source support member so as to separate the photocatalytic filter from the light emitting diode.

According to one embodiment, the photocatalytic filter may include a plurality of photocatalytic filters.

According to one embodiment, the plurality of photocatalytic filters may be placed in the same plane.

According to one embodiment, the frame may include a rib disposed between the plurality of photocatalytic filters.

According to one embodiment, a distance between the plurality of photocatalytic filters may be the same as a width of the rib.

According to one embodiment, the light emitting diode may have an angle of beam spread of 120 degrees or less.

According to one embodiment, a ratio (D/L) of a diameter D of the photocatalytic filter to a distance L between the photocatalytic filter and the light emitting diode may range from 3.46 to 3.50.

According to one embodiment, the frame may include a first frame and a second frame, and the photocatalytic filter may be disposed between the first frame and the second frame.

According to one embodiment, the photocatalytic filter may include a plurality of photocatalytic filters, and the first frame and the second frame may include a first rib and a second rib, respectively, the first rib and the second rib each being disposed between the plurality of photocatalytic filters.

According to one embodiment, the light source support member may include a plurality of light source support members, and the light source unit may further include an auxiliary member coupled to the plurality of light source support members.

According to one embodiment, the auxiliary member may include a metal to dissipate heat generated from the light emitting diode and the light source support members.

According to one embodiment, the light source unit may include a plurality of light emitting diodes disposed on the light source support member.

According to one embodiment, the frame may further include a coupling member connecting the frame to the light source support member, the coupling member being used to adjust a distance between the frame and the light source support member.

According to one embodiment, the light emitting diode may include a plurality of light emitting diodes separated from one another with the photocatalytic filter disposed therebetween.

According to one embodiment, the photocatalytic filter may include: a plurality of sintered beads having a surface coated with a photocatalytic material; and pores disposed between the beads.

According to one embodiment, the bead may include at least one selected from the group of alumina ($Al_2O_3$), silicon oxide ($SiO_2$), zirconia ($ZrO_2$), silicon nitride ($Si_3N_4$), silicon carbide (SiC), and combinations thereof.

According to one embodiment, the photocatalytic material may include at least one selected from the group of titanium dioxide ($TiO_2$), zirconia ($ZrO_2$), zinc oxide (ZnO), tungsten oxide ($WO_3$), and tin oxide ($SnO_2$).

According to one embodiment, the light emitting diode may emit light having a wavelength in the UV wavelength band.

According to one embodiment, the fluid treatment device may further include: a blower forcing the fluid toward the photocatalytic filter.

According to one embodiment, the photocatalytic filter and the light source unit may include a plurality of photocatalytic filters and a plurality of light source units, respectively, the plurality of photocatalytic filters and the plurality of light source units being alternately arranged in series.

According to embodiments of the present invention, the fluid treatment device can remove air pollutants at the source.

In addition, according to embodiments of the present invention, the fluid treatment device can provide sterilization of indoor air and can also sterilize and purify the interior thereof when in operation.

Further, according to embodiments of the present invention, the fluid treatment device has improved purification efficiency.

Furthermore, according to embodiments of the present invention, the fluid treatment device can be used in large air conditioners.

BRIEF DESCRIPTION OF DRAWINGS

FIG. 5B is an exploded perspective view of the fluid treatment device of FIG. 5A.

FIG. 6 is an exploded perspective view of a fluid treatment device according to yet another embodiment.

DETAILED DESCRIPTION OF EMBODIMENTS

Figure 1:
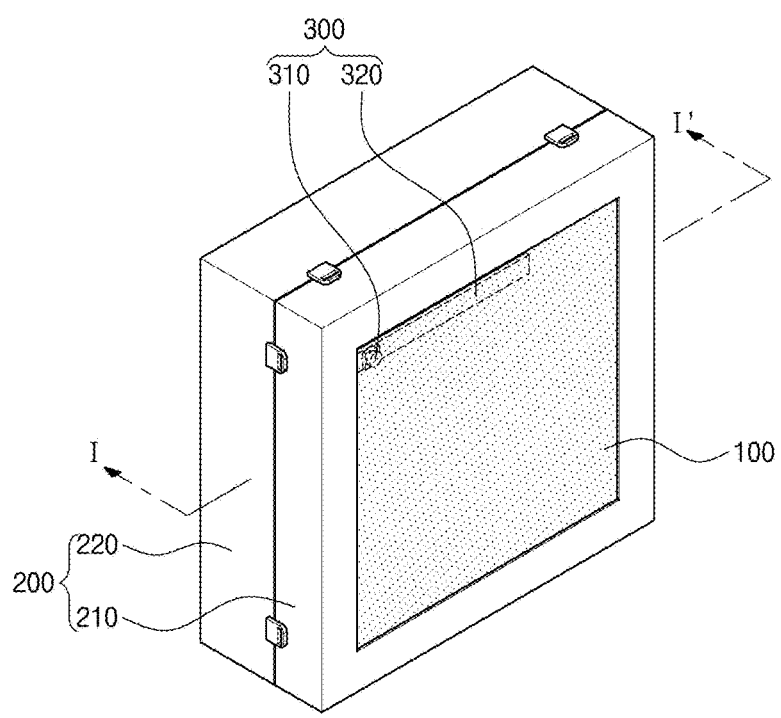
FIG. 1 is a perspective view of a fluid treatment device according to one embodiment of the present invention.

The present invention may be implemented in various ways and certain embodiments will be described in detail with reference to the accompanying drawings. However, it should be understood that the present invention is not limited to the following embodiments and includes all modifications, variations, alterations, and equivalents fallowing within the spirit and scope of the present invention.

Like components will be denoted by like reference numerals throughout the specification. It should be noted that the drawings may be exaggerated in thickness of lines or size of components for descriptive convenience and clarity only. It will be understood that, although the terms "first," "second," "A," "B," and the like may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a "first" element or component discussed below could also be termed a "second" element or component, or vice versa, without departing from the scope of the present invention. As used herein, the singular forms "a," "an," and "the" are intended to include the plural forms as well, unless the context clearly indicates otherwise.

It will be understood that the terms "includes," "comprises," "including" and/or "comprising," when used in this specification, specify the presence of stated features, steps, operations, elements, and/or components, but do not preclude the presence or addition of one or more other features, steps, operations, elements, components, and/or groups. In addition, when a layer, film, region, or panel is referred to as being "on" another layer, film, region, or panel, it may be directly on the other layer, film, region, or panel, or intervening layers, films, regions, or panels may be present. In addition, when a layer, film, region, or panel is referred to as being "formed on" another layer, film, region, or panel, it may be formed on an upper, lower, or side surface of the other layer, film, region, or panel. Further, when a layer, film, region, or panel is referred to as being "under" another layer, film, region, or panel, it may be directly under the other layer, film, region, or panel, or intervening layers, films, regions, or panels may be present.

Hereinafter, exemplary embodiments of the present invention will be described in detail with reference to the accompanying drawings.

FIG. 1 is a perspective view of a fluid treatment device according to one embodiment of the present invention.

A fluid treatment device according to this embodiment includes a light source and a photocatalytic filter arranged so as to maximize purification efficiency. In addition, the fluid treatment device according to this embodiment can remove pollutants at the source.

Referring to FIG. 1, the fluid treatment device includes a photocatalytic filter 100, a frame 200, and a light source unit 300.

The photocatalytic filter 100 purifies a fluid passing through the photocatalytic filter 100, for example, air. Accordingly, pollutants contained in air can be removed by the photocatalytic filter 100. Specifically, the photocatalytic filter 100 can physically and chemically purify air.

First, for physical purification, pollutants in air may be removed by being adsorbed onto the photocatalytic filter 100. To this end, the photocatalytic filter 100 may include a plurality of pores.

Next, for chemical purification, the photocatalytic filter 100 may decompose and sterilize pollutants. The photocatalytic filter 100 has a surface coated with a photocatalyst that can be activated when illuminated with light. When the photocatalyst is activated, a photocatalytic reaction occurs, causing decomposition and sterilization of pollutants.

Here, the photocatalytic reaction may refer to a reaction in which superoxide anions ($O_2^-$) and/or hydroxyl radicals (OH·) are produced from water and oxygen in air. The produced superoxide anions ($O_2^-$) and/or hydroxyl radicals (OH·) can decompose and sterilize organic pollutants and inorganic pollutants and can decompose and destroy germs, such as viruses or bacteria.

Specifically, organic pollutants can be decomposed into water and carbon dioxide by reacting with superoxide anions ($O_2^-$) and/or hydroxyl radicals (OH·). In addition, inorganic pollutants can be decomposed into an oxide, such as nitrogen oxide. Further, germs such as bacteria can be disabled by reacting with superoxide anions ($O_2^-$) and/or hydroxyl radicals (OH·). Specifically, superoxide anions ($O_2^-$) and/or hydroxyl radicals (OH·) can disable germs, such as bacteria, by reacting with DNA and a cell membrane thereof.

Through chemical purification as described above, pollutants can be removed at the source. Typical filters provide only physical filtration and thus fail to remove pollutants at the source. In particular, bacteria are just temporarily inactivated and do not die over time when adsorbed to such a typical filter. That is, physical adsorption of bacteria onto the filter is just a temporary measure, since the bacteria can be reactivated at any time by contacting a living creature. The fluid treatment device according to this embodiment can remove bacteria at the source by disabling the bacteria.

The photocatalytic filter 100 is held by the frame 200. Accordingly, the frame 200 can prevent the photocatalytic filter 100 from being loose or moving when such movement is not needed or undesirable. Specifically, the frame 200 prevents the photocatalytic filter 100 from being damaged by an unintended movement due to a fluid and the like passing through the photocatalytic filter 100. In addition, the frame 200 protects the photocatalytic filter 100 from external impact.

In some embodiments, the frame 200 may include a first frame 210 and a second frame 220.

The photocatalytic filter 100 may be disposed between the first frame 210 and the second frame 220. The photocatalytic filter 100 disposed between the first frame 210 and the second frame 220 can be secured and protected by fastening the first frame 210 to the second frame 220.

Accordingly, the first frame 210 and the second frame 220 may be matched in shape with each other. The first frame 210 and the second frame 220 may have any suitable shapes without limitation. However, in order to effectively hold the photocatalytic filter 100, each of the first frame 210 and the second frame 220 may have a shape corresponding to the photocatalytic filter 100. For example, when the photocatalytic filter 100 has a cuboid shape, as shown in the drawings, each of the first frame 210 and the second frame 220 may have a shape corresponding to sides of the cuboid shape. However, it will be understood that other implementations are possible and the first frame 210 and the second frame 220 may have various other shapes.

Each of the first frame 210 and the second frame 220 has an opening at the front side thereof. The photocatalytic filter 100 may be exposed through the openings of the first frame 210 and the second frame 220. Accordingly, the fluid flows out of the fluid treatment device through the openings of the first frame 210 and the second frame 220 and the photocatalytic filter 100 disposed in the openings.

In order to prevent the fluid from leaving the fluid treatment device without passing through the photocatalytic filter 100, the photocatalytic filter 100 may be tightly fitted into the first frame 210 and the second frame 220.

Figure 2:
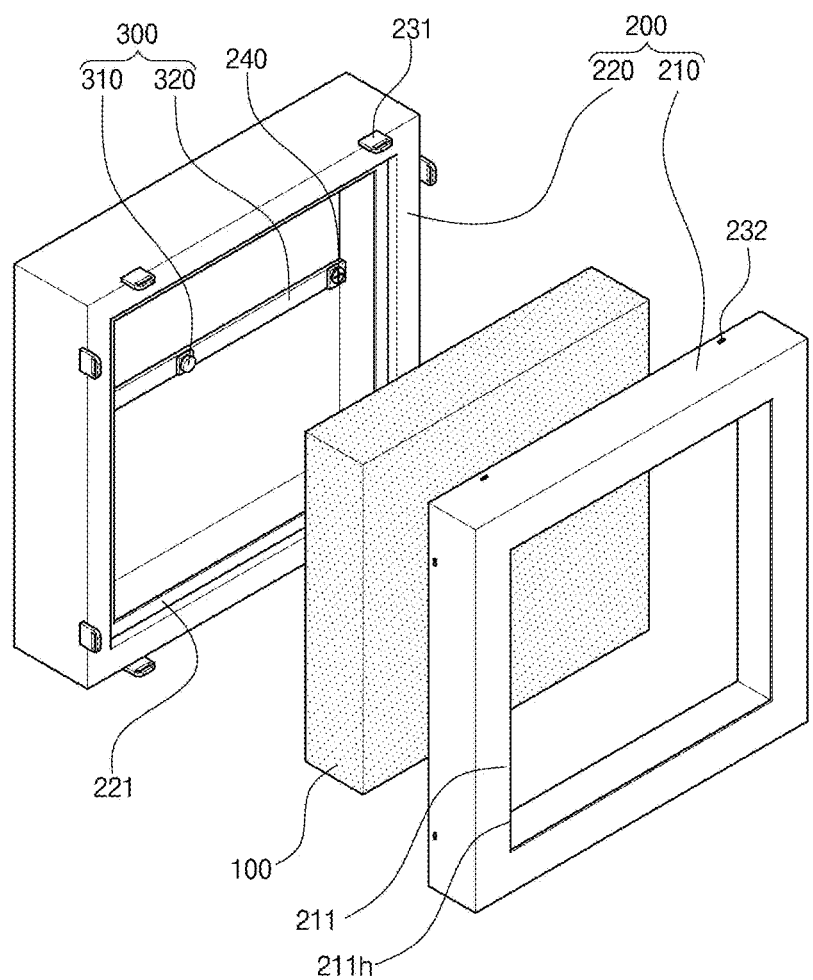
FIG. 2 is an exploded perspective view of the fluid treatment device of FIG. 1.

The frame 200 is coupled to the light source unit 300. The light source unit 300 is disposed in the fluid treatment device by being coupled to the frame 200. The light source unit 300 includes a light emitting diode 310 and a light source support member 320. In FIG. 1, the light source unit 300 is illustrated in a dotted line to indicate that the light source unit 300 is coupled to the frame 200 and not on the photocatalytic filter 100 as illustrated in FIG. 2. The positioning and the arrangement as shown in FIG. 1 is by way of example only and positioning at various other locations is available.

The light emitting diode 310 is disposed on the light source support member 320 to emit light toward the photocatalytic filter 100. The photocatalytic filter 100 is activated by the light emitted from the light emitting diode 310.

Accordingly, the light emitting diode 310 emits light having a wavelength that can activate the photocatalytic filter 100. The wavelength of light emitted from the light emitting diode 310 may vary depending upon the type of photocatalytic filter 100. For example, when the photocatalytic filter 100 includes a titanium oxide ($TiO_2$) photocatalyst, the light emitted from the light emitting diode 310 may include UV light.

The light source support member 320 supports the light emitting diode 310. The light emitting diode 310 is secured to the light source support member 320 in a manner that maximizes the area over which the photocatalytic filter 100 is illuminated with light therefrom.

The light source support member 320 may include an interconnect (not shown) electrically connected to the light emitting diode 310. The interconnect may connect the light emitting diode 310 to a power supply or a controller. The interconnect may be disposed inside the light source support member 320 so as not be damaged by the fluid passing through the fluid treatment device.

The light source support member 320 is coupled to the frame 200. Specifically, the light source support member 320 may be coupled to the frame 200 so as to separate the photocatalytic filter 100 from the light emitting diode 310. That is, the light source support member 320 may be coupled to the frame 200 such that the light emitting diode 310 is separated from the photocatalytic filter 100 by an optimal distance. More specifically, through the coupling between the light source support member 320 and the frame 200, the light emitting diode 310 can be disposed so as to maximize the area over which the photocatalytic filter 100 is illuminated with light therefrom while providing sufficient irradiance to activate the photocatalytic filter 100.

Now, description of configuration of each component described above will be given in more detail.

FIG. 2 is an exploded perspective view of the fluid treatment device of FIG. 1.

Referring to FIG. 2, the frame 200 includes the first frame 210 and the second frame 220 fastened to each other, and the photocatalytic filter 100 is disposed between the first frame 210 and the second frame 220.

The first frame 210 and the second frame 220 have a first edge 211 and a second edge 221, respectively. The first edge 211 and the second edge 221 protrude inwardly of the openings of the first frame 210 and the second frame 220, respectively. Accordingly, the first edge 211 and the second edge 221 serve to prevent the photocatalytic filter 100 from escaping from the frame in a direction in which the fluid flows.

Regions of the first frame 210 and the second frame 220 which are not formed with the first edge 211 and the second edge 221 may include openings, respectively. For example, a region of the first frame 210 which is not formed with the first edge 211 may be defined as a first opening 211h.

In some embodiments, the first opening 211h has a smaller size than the photocatalytic filter 100. Accordingly, the photocatalytic filter 100 coupled to the frame 200 can be prevented from moving out of the first opening 211h. However, the first opening 211h may be of a size that does not interfere with the flow of the fluid through the photocatalytic filter 100.

In some embodiments, the fluid treatment device may further include an auxiliary filter inserted between the first frame 210 and the photocatalytic filter 100, although not shown in the drawings. The auxiliary filter may include a pre-filter, a HEPA filter, a medium filter, a ULPA filter, an activated carbon filter, and the like.

The first frame 210 and the second frame 220 may include a second frame securing portion 232 and a first frame securing portion 231, respectively. The first and second frame securing portions 231, 232 may be matched in shape with each other to be easily coupled to each other. Through coupling between the first and second frame securing portions 231, 232, the first frame 210 and the second frame 220 can be securely coupled to each other. Coupling between the first and second frame securing portions 231, 232 may be established by any suitable fastening method without limitation. For example, coupling between the first and second frame securing portions 231, 232 may be established by clip-engagement, as shown in FIG. 2, or may be established by various other coupling methods, such as sliding engagement or thread-engagement.

The first and second frame securing portions 231, 232 may be detachably coupled to each other. Accordingly, upon replacing the light emitting diode 310 or the photocatalytic filter 100, the first and second frame securing portions 231, 232 can be separated from each other prior to perform replacement.

The first and second frame securing portions 231, 232 may include a plurality of first securing portions 231 and a plurality of second frame securing portions 232, respectively. Specifically, the first and second frame securing portions 231, 232 may include a plurality of first securing portions 231 and a plurality of second frame securing portions 232 arranged along outer surfaces of the first frame 210 and the second frame 220, respectively. In this way, the first frame 210 and the second frame 220 can be coupled to each other in a highly stable manner.

The light source unit 300 may be coupled to the frame 200 via a coupling member 240. Specifically, the second frame 220 may be coupled to the light source support member 320 via the coupling member 240. Here, the coupling member 240 may employ any suitable coupling method, such as screw-engagement as shown in FIG. 2, clip-engagement, sliding engagement, or clamp-engagement.

In the screw-engagement as shown in FIG. 2, the coupling member 240 may be configured to pass through both a protrusion formed on the second frame 220 and the light source support member 320. Here, the protrusion may be formed on the second frame 220 such that the light emitting diode 310 disposed on the light source support member 320 is separated from the photocatalytic filter 100 by an optimal distance. Accordingly, the second edge 221 adjoining the photocatalytic filter 100 may be separated from the protrusion.

The light emitting diode 310 may be positioned to face the photocatalytic filter 100. That is, the light emitting diode 310 may be disposed on a surface of the light source support member 320 which faces the photocatalytic filter 100.

In addition, the fluid treatment device may further include a reflective member disposed on the surface of the light source support member 320 on which the light emitting diode 310 is disposed. The reflective member reflects light emitted from the light emitting diode 310 toward the photocatalytic filter 100. In this way, the irradiance delivered to the photocatalytic filter 100 can be increased.

Figure 3:
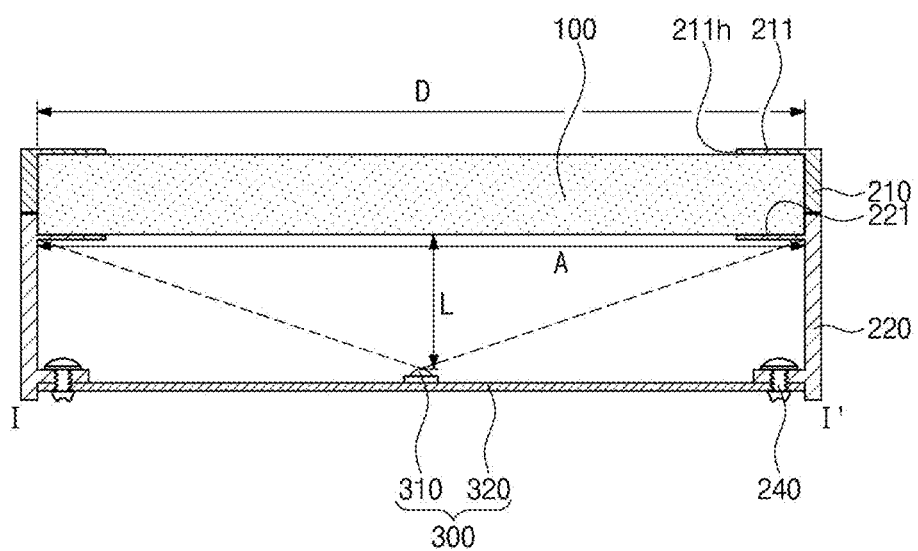
FIG. 3 is a sectional view of the fluid treatment device taken along line I-I of FIG. 1.

FIG. 3 is a sectional view of the fluid treatment device taken along line I-I of FIG. 1. In FIGS. 1 through 3, the arrangement and positioning of the light emitting diode 310 on the light source support member 320 are illustrated in different views by way of example and various other arrangements are available.

Referring to FIG. 3, with the photocatalytic filter 100, the first frame 210, the second frame 220 and the light source unit 300 coupled to one another, the light emitting diode 310 is separated from the photocatalytic filter 100 by an optimal distance L.

Here, the optimal distance L is a distance between the light emitting diode 310 and the photocatalytic filter 100, which can maximize both the irradiance delivered to the photocatalytic filter 100 and the area over which the photocatalytic filter 100 is illuminated. Here, the irradiance delivered to the photocatalytic filter 100 may be greater than or equal to minimal irradiance for activation of the photocatalytic filter 100. The light emitting diode 310 is located at the center of the light source support member 320 in the cross-sectional view as shown in FIG. 3. However, the embodiments of the present disclosure are not limited thereto. Regardless of the location of the light emitting diode 310 on the light source support member 320, the identical optimal distance L may be maintained due to the separation between the light emitting diode 310 and the photocatalytic filter 100. As will be described in detail below, two or more light emitting didoes may be used as a light source. In such embodiments, the positioning and arrangements of each light emitting diode may vary.

When the light emitting diode 310 is separated from the photocatalytic filter 100 by the optimal distance L, the photocatalytic filter 100 may be illuminated over an area as large as an illumination region A as marked with an arrow in FIG. 3. Here, the diameter of the illumination region A may be substantially the same as the diameter D of the photocatalytic filter. Accordingly, the photocatalytic filter 100 can be illuminated over substantially the entire area thereof.

A ratio (D/L) of the diameter D of the photocatalytic filter to the optimal distance L may range from about 3.46 to about 3.50. Within this range, sufficient irradiance to activate the photocatalytic filter 100 can be delivered over substantially the entire area of the photocatalytic filter 100.

The light emitting diode 310 may have an angle of beam spread of 120 degrees or less. Within this range of angle of beam spread, sufficient irradiance to activate the photocatalytic filter 100 can be delivered over as large an area as possible of the photocatalytic filter.

In some embodiments, the frame 200 may be coupled to the light source support member 320 so as to separate the photocatalytic filter 100 from the light emitting diode 310 by the optimal distance L. Coupling the frame 200 to the light source support member 320 in this manner can provide structural stability allowing the optimal distance L to be maintained between the photocatalytic filter 100 and the light emitting diode 310. Accordingly, the fluid treatment device can have improved fluid treatment efficiency.

The second edge 221 (see FIG. 2) may be optically transparent. Accordingly, light emitted from the light emitting diode 310 can arrive at the photocatalytic filter 100 without being blocked by the second edge 221. Here, the expression "optically transparent" includes not only "capable of transmitting light in every wavelength band" but also "capable of transmitting light in a specific wavelength band."

In the above embodiment, the light source unit 300 has been described as including one light emitting diode 310. However, it will be understood that other implementations are possible and the light source unit 300 may include a plurality of light emitting diodes 310. The embodiments of the present disclosure will now be described using an example in which the light source unit 300 includes a plurality of light emitting diodes 310.

Figure 4A:
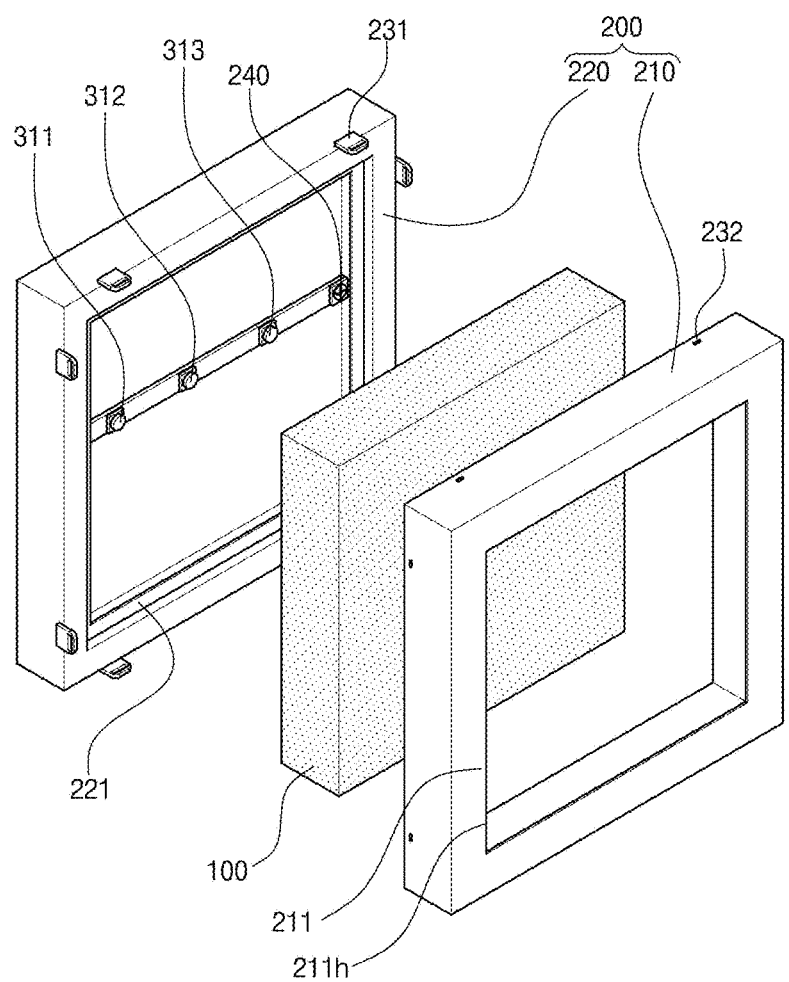
FIG. 4A is an exploded perspective view of a fluid treatment device according to another embodiment.
Figure 4B:
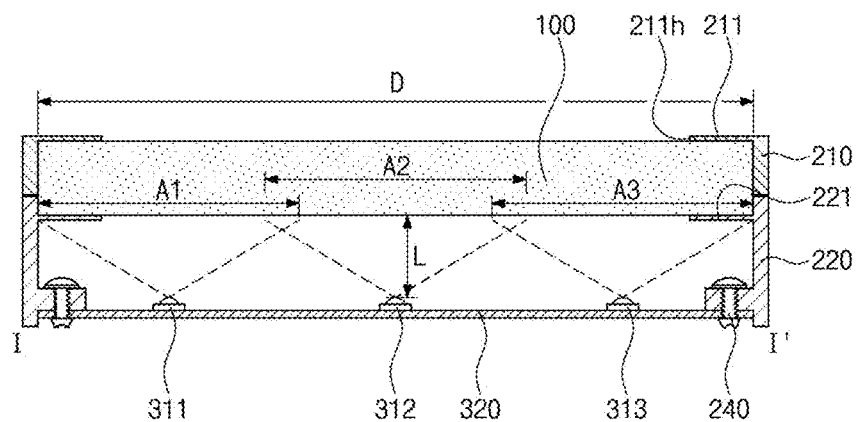
FIG. 4B is a sectional view of the fluid treatment device of FIG. 4A.

FIG. 4A is an exploded perspective view of a fluid treatment device according to another embodiment, and FIG. 4B is a sectional view of the fluid treatment device of FIG. 4A.

Referring to FIG. 4A and FIG. 4B, the fluid treatment device according to this embodiment includes first to third light emitting diodes 311, 312, 313.

Here, the first light emitting diode 311 illuminates the photocatalytic filter over an area as large as a first illumination region A1 and the second light emitting diode 312 illuminates the photocatalytic filter over an area as large as a second illumination region A2. The third light emitting diode 313 illuminates the photocatalytic filter over an area as large as a third illumination region A3.

The first to third light emitting diodes 311, 312, 313 may be arranged so as to avoid overlapping between the first to third illumination regions A1, A2, A3. However, it will be understood that other implementations are possible and the first to third illumination regions A1, A2, A3 may partially overlap one another. The first to third light emitting diodes 311, 312, 313 may be manually arranged so as to allow the entire area of the photocatalytic filter 100 to be illuminated while minimizing overlap between the first to third illumination regions A1, A2, A3.

The sum of the diameters of the first to third illumination regions A1, A2, A3 may be greater than or equal to the diameter D of the photocatalytic filter. Accordingly, sufficient irradiance to activate the photocatalytic filter 100 can be delivered over the entire area of the photocatalytic filter 100.

When the light source unit includes the first light emitting diode 311, the second light emitting diode 312, and the third light emitting diode 313, as shown in FIGS. 4A and 4B, the optimal distance L may be relatively short. Specifically, when the light source unit includes the plurality of light emitting diodes, the optimal distance L may be shorter than when the light source unit includes one light emitting diode.

The irradiance delivered to the photocatalytic filter 100 may increase with deceasing distance between the photocatalytic filter 100 and the first to third light emitting diodes 311, 312, 313. Accordingly, light having an energy greater than or equal to minimal activation energy required to activate the photocatalytic filter 100 can be more easily delivered to the photocatalytic filter 100. In addition, when light emitted from the first to third light emitting diodes 311, 312, 313 includes UV light, the fluid treatment device can have improved sterilization performance.

In FIGS. 4A and 4B, the first to third light emitting diodes 311, 312, 313 are shown as arranged side by side on the same line. However, it will be understood that other implementations are possible and the first to third light emitting diodes 311, 312, 313 may be arranged in various other manners depending upon the shape of the photocatalytic filter 100 and characteristics of the light emitting diode.

In addition, since the light emitting diode 310 is detachably disposed on the light source support member 320, the light emitting diode 310 can be manually detached from the light source support member 320 and be reattached to a desired location, as needed. Accordingly, when a certain light emitting diode 310 has a problem, a user can easily replace only the problematic light emitting diode 310 without needing to replace the entire light source unit 300.

Hereinbefore, a fluid treatment device including one photocatalytic filter 100 and a plurality of light emitting diodes 311, 312, 313 has been described. However, it will be understood that other implementations are possible and a fluid treatment device according to the present invention may also include a plurality of photocatalytic filters 100. Hereinafter, the present invention will be described using an example in which a plurality of photocatalytic filters 100 is provided.

Figure 5A:
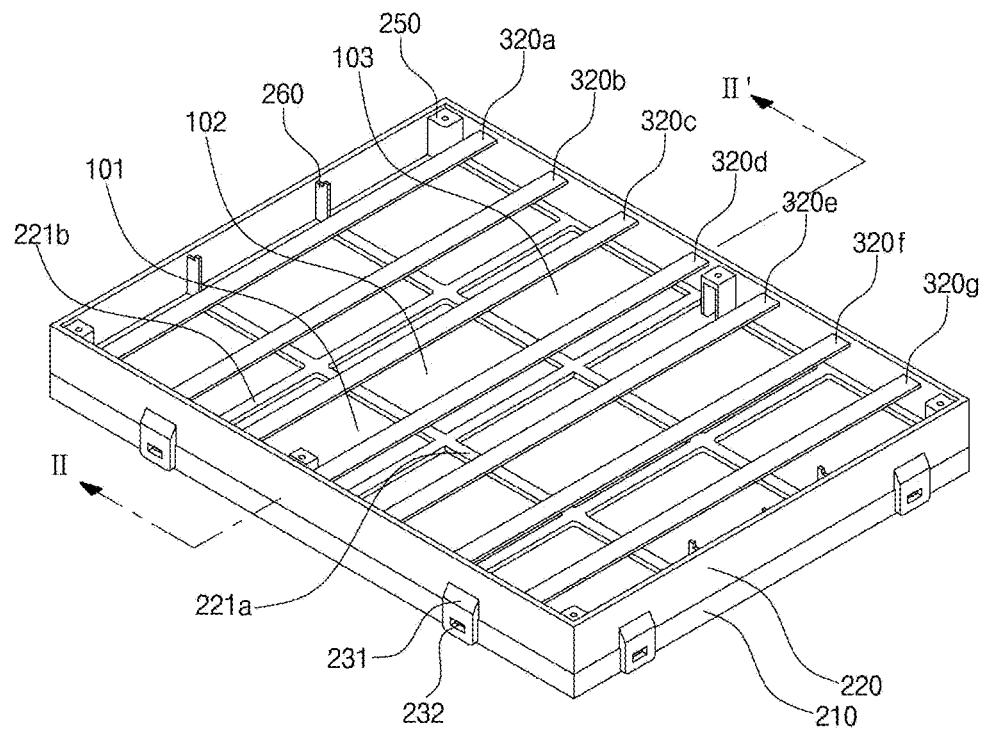
FIG. 5A is a perspective view of a fluid treatment device according to a further embodiment.
Figure 5C:
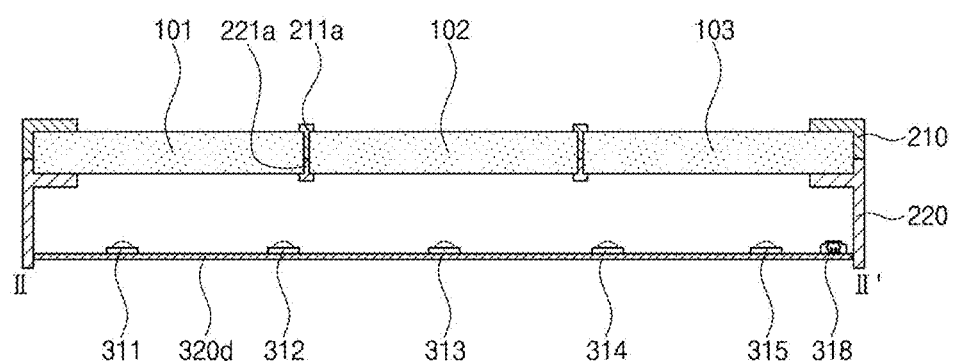
FIG. 5C is a sectional view of the fluid treatment device taken along line II-II' of FIG. 5A.

FIG. 5A is a perspective view of a fluid treatment device according to a further embodiment of the present invention and FIG. 5B is an exploded perspective view of the fluid treatment device of FIG. 5A. FIG. 5C is a sectional view of the fluid treatment device taken along line II-II' of FIG. 5A.

Referring to FIG. 5A to FIG. 5C, a fluid treatment device according to this embodiment includes first to third photocatalytic filters 101, 102, 103 arranged side by side in a row. In addition, each of the first to third photocatalytic filters 101, 102, 103 may include a plurality of photocatalytic filters arranged in a column. Accordingly, the first to third photocatalytic filters may be arranged in a matrix in the same plane. However, it will be understood that this arrangement is given by way of example only and the first to third photocatalytic filters 101, 102, 103 may be arranged in various other forms depending upon the shapes thereof.

The frame 200 may include a rib holding the first to third photocatalytic filters 101, 102, 103. Specifically, the first frame 210 and the second frame 220 may include a first rib 211a, 211b and a second rib 221a, 221b, respectively, wherein the first rib 211a, 211b and the second rib 221a, 221b are disposed between the first to third photocatalytic filters 101, 102, 103. The first rib 211a, 211b may be integrally formed with a first edge formed at one side of the first frame 210, as shown in FIG. 5B. The second rib 221a, 221b may be integrally formed with a second edge formed at one side of the second frame 220, as shown in FIG. 5B.

The first rib 211a, 211b may be divided into a first longitudinal rib 211a and a first transverse rib 211b according to which direction the rib extends. Similarly, the second rib 221a, 221b may be divided into a second longitudinal rib 221a and a second transverse rib 221b according to which direction the rib extends. Here, the first and second longitudinal ribs 211a, 221a do not necessarily cross the first and second transverse ribs 211b, 221b at right angles, respectively. The first and second longitudinal ribs 211a, 221a may cross the first and second transverse ribs 211b, 221b at acute angles or obtuse angles, respectively, depending upon the shapes of the first through the third photocatalytic filters 101, 102, 103.

As shown in FIG. 5A, the widths of the first and second longitudinal ribs 211a, 221a and the first and second transverse ribs 211b, 221b may correspond to the separation distance between neighboring photocatalytic filters 101, 102, 103. In some embodiments, the widths of the ribs 211a, 221a, 211b, 221b may be the same as the separation distance between neighboring photocatalytic filters 101, 102, 103. Accordingly, the first to the third photocatalytic filters 101, 102, 103 can be coupled to the first frame 210 and the second frame 220 with substantially no gaps in between. In this way, structural stability can be secured even when the fluid treatment device includes the plurality of photocatalytic filters 101, 102, 103.

In addition, the first rib 211a, 211b may have a protrusion at an upper end thereof, and the second rib 221a, 221b may have a protrusion at a lower end thereof. The protrusions serve to prevent the first to third photocatalytic filters 101, 102, 103 from escaping from the frame in a direction in which the fluid flows.

The first rib 211a, 211b and the second rib 221a, 221b may be optically transparent not to block light emitted from the light emitting diode. Here, the expression "optically transparent" includes not only "capable of transmitting light in every wavelength band" but also "capable of transmitting light in a specific wavelength band."

The second frame 220 may further include an auxiliary member coupling portion 250 and a reinforcement member 260. The auxiliary member coupling portion 250 may be coupled to an auxiliary member of the light source unit. The auxiliary member coupling portion 250 will be described further below.

The reinforcement member 260 serves to improve structural stability of the second frame 220. When the second frame 220 is increased in size due to increase in number of photocatalytic filters provided to the fluid treatment device, structural rigidity of the second frame 220 can be improved by providing the reinforcement member 260 to the second frame 220.

The light source unit may include first to seventh light source support members 320a to 320g. The first to seventh light source support members 320a to 320g may be arranged at the same interval, or the distance between some neighboring ones of the first to seventh light source support members may be different from the distance between the other neighboring ones. For example, the first to seventh light source support members 320a to 320g may be grouped in pairs or as a trio. In this case, the distance between the first light source support member 320a and the second light source support member 320b may be shorter than the distance between the second light source support member 320b and the third light source support member 320c.

The first to seventh light source support members 320a to 320g may be arranged so as to allow sufficient irradiance to activate the photocatalyst to be delivered over as large an area as possible of each of the first to third photocatalytic filters 101, 102, 103.

Each of the first to seventh light source support members 320a to 320g may include a plurality of light emitting diodes. For example, the fourth light source support member 320d may include first to fifth light emitting diodes 311 to 315.

The first to fifth light emitting diodes 311 to 315 are spaced apart from one another. Here, the first to fifth light emitting diodes 311 to 315 may be arranged at the same or different intervals. For example, among the light emitting diodes shown in the drawings, the first light emitting diode 311 and the second light emitting diode 312 may be positioned relatively close to each other to be matched with the first photocatalytic filter 101. Accordingly, the distance between the second light emitting diode 312 and the third light emitting diode 313 may be relatively long.

The first to fifth light emitting diodes 311 to 315 may be arranged so as to allow sufficient irradiance to activate the photocatalyst to be delivered over as large an area as possible of each of the first through the third photocatalytic filters 101, 102, 103.

In other embodiments, the first to seventh light source support members 320a to 320g are not necessarily provided with the same number of light emitting diodes. For example, the fourth light source support member 320d may be provided with five light emitting diodes, whereas the third light source support member 320c may be provided with only three light emitting diodes.

In addition, in other embodiments, the light emitting diodes provided to the first to seventh light source support members 320a to 320g are not necessarily arranged in a matrix. For example, the plurality of light emitting diodes may also be arranged in zigzag form.

The first to seventh light source support members 320a to 320g and the first to fifth light emitting diodes 311 to 315 may be arranged in various forms depending upon arrangement of the first to the third photocatalytic filters 101, 102, 103.

In addition, the first to seventh light source support members 320a to 320g and the first to the fifth light emitting diodes 311 to 315 may be arranged so as not to be hidden by the first rib 211a, 211b and the second rib 221a, 221b. For example, in plan view, the first to seventh light source support members 320a to 320g may be arranged alternately with the first transverse rib 211b and the second transverse rib 221b so as not to overlap the first transverse rib 211b and the second transverse rib 221b.

Each of the first to seventh light source support members 320a to 320g may include a connector 318 disposed at one side thereof. For example, the fourth light source support member 320d may include a connector 318 disposed at a rightmost side thereof. The connector 318 may be electrically connected to the first to fifth light emitting diodes 311 to 315 via an interconnect. Here, the interconnect may be disposed inside the fourth light source support member 320d. Further, the connector may serve as a bridgehead connecting the first to fifth light emitting diodes 311 to 315 to an external power supply or a controller.

In some embodiments, the fluid treatment device may include a plurality of photocatalytic filters. Since the plurality of photocatalytic filters are held by the first frame 210 and the second frame 220 each including ribs, the fluid treatment device can have structural stability. In addition, in order to activate the plurality of photocatalytic filters, the light source unit may include a plurality of light source support members and a plurality of light emitting diodes. In this way, all the photocatalytic filters included in the fluid treatment device can be activated.

As described above, according to this embodiments of the present disclosure, the fluid treatment device can be structurally stable and highly efficient in fluid treatment even when including a plurality of photocatalytic filters. Thus, the fluid treatment device according to the embodiments can be used in large-scale air conditioners. Specifically, since a fluid treatment rate per unit time can be increased by arranging the plurality of photocatalytic filters in the same plane, the fluid treatment device according to the embodiments can be used in large-scale air conditioners requiring a high fluid treatment rate.

A ceramic photocatalytic filter can only be scaled up to a certain degree. This is because a large photocatalytic filter is likely to suffer warpage during manufacture thereof. In addition, increasing the thickness of the photocatalytic filter to prevent warpage of the photocatalytic filter can cause an excessively low flow rate of a fluid through the photocatalytic filter. Therefore, there may be limitations in scaling up the photocatalytic filter beyond a certain degree. According to the embodiments described herein since a plurality of photocatalytic filters can be disposed in the same plane, a fluid treatment rate per unit time can be increased without using a large photocatalytic filter.

FIG. 6 is an exploded perspective view of a fluid treatment device according to yet another embodiment.

Referring to FIG. 6, a plurality of photocatalytic filters 100 is provided as in the above embodiment. However, the photocatalytic filters 100 each have a rectangular shape extending in one direction.

In addition, the first frame 210 and the second frame 220 may correspond in shape to the photocatalytic filters 100. Specifically, the first rib 211a of the first frame 210 and the second rib 221a of the second frame 220 may be configured to surround each of the rectangular photocatalytic filters 100. In this case, each of the first rib 211a and the second rib 221a may include only a transverse rib without a rib crossing the transverse rib.

In the above embodiments, the light emitting diodes are arranged to illuminate one surface of the photocatalytic filter. However, it will be understood that other implementations are possible and the light emitting diodes may be arranged in various other manners, as needed. For example, the light emitting diodes may be arranged to illuminate both surfaces of the photocatalytic filter.

Figure 7A:
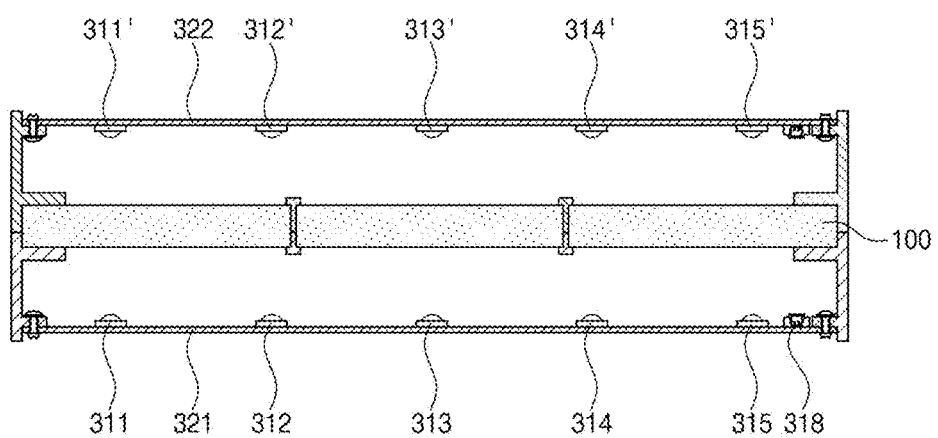
FIG. 7A is a sectional view of a fluid treatment device according to yet another embodiment.
Figure 7B:
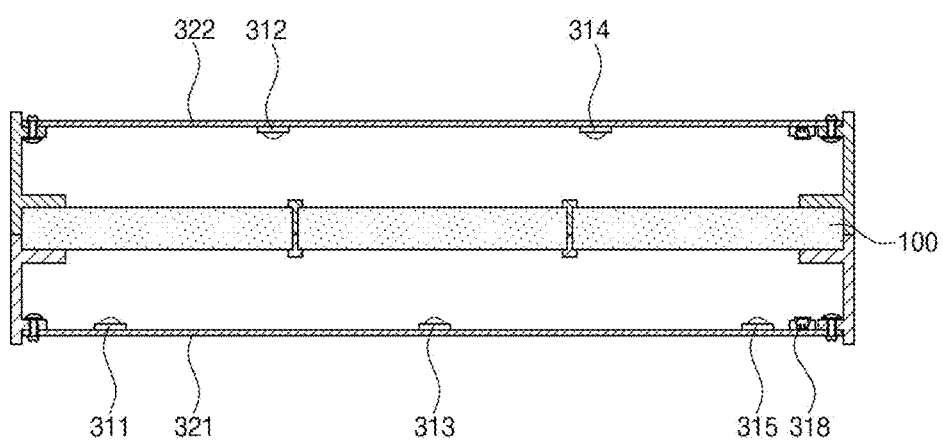
FIG. 7B is another sectional view of the fluid treatment device according to yet another embodiment.

FIGS. 7A and 7B are sectional views of a fluid treatment device according to yet another embodiment of the present disclosure.

Referring to FIG. 7A, the light source unit includes an upper light source support member 321 and a lower light source support member 322. The upper light source support member 321 includes first to fifth light emitting diodes 311 to 315, and the lower light source support member 322 includes sixth to tenth light emitting diodes 311' to 315'. The first to fifth light emitting diodes 311 to 315 may be positioned to face the sixth to tenth light emitting diodes 311' to 315', respectively. However, it will be understood that other implementations are possible and the light emitting diodes may be arranged in various other manners.

Referring to FIG. 7B, the upper light source support member 321 includes first, third, and fifth light emitting diodes 311, 313, 315 and the lower light source support member 322 includes second and fourth light emitting diodes 312, 314. The first, third, and fifth light emitting diodes 311, 313, 315 and the second and fourth light emitting diodes 312, 314 are alternately arranged relative to one another so as not to overlap one another in plan view.

In other words, the first, third, and fifth light emitting diodes 311, 313, 315 and the second and fourth light emitting diodes 312, 314 are spaced apart from each other in the horizontal direction such that each of the first, third, and fifth light emitting diodes 311, 313, 315 is not aligned with each of the second and fourth light emitting diodes 312, 314 in the vertical direction, as illustrated in FIG. 7B.

When the light source unit includes the upper light source support member 321 and the lower light source support member 322, as shown in FIG. 7A and FIG. 7B, both surfaces of the photocatalytic filter 100 can be illuminated. Accordingly, the photocatalytic filter 100 can be illuminated over a larger area. As a result, a larger amount of the photocatalyst can be activated, thereby allowing improvement in fluid treatment capacity per unit time.

Figure 8A:
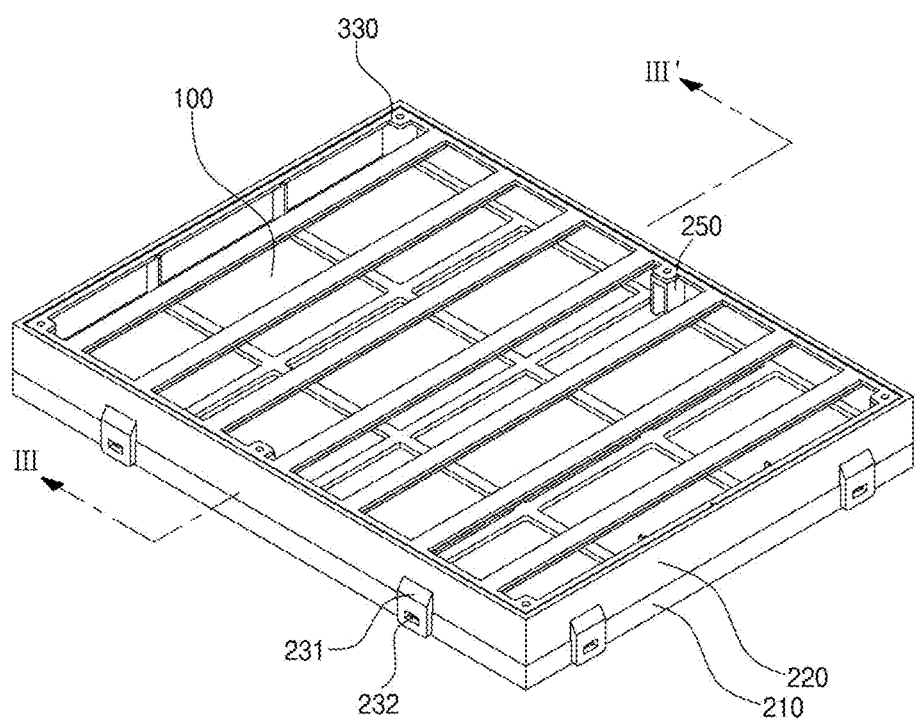
FIG. 8A is a perspective view of a fluid treatment device according to yet another embodiment.
Figure 8B:
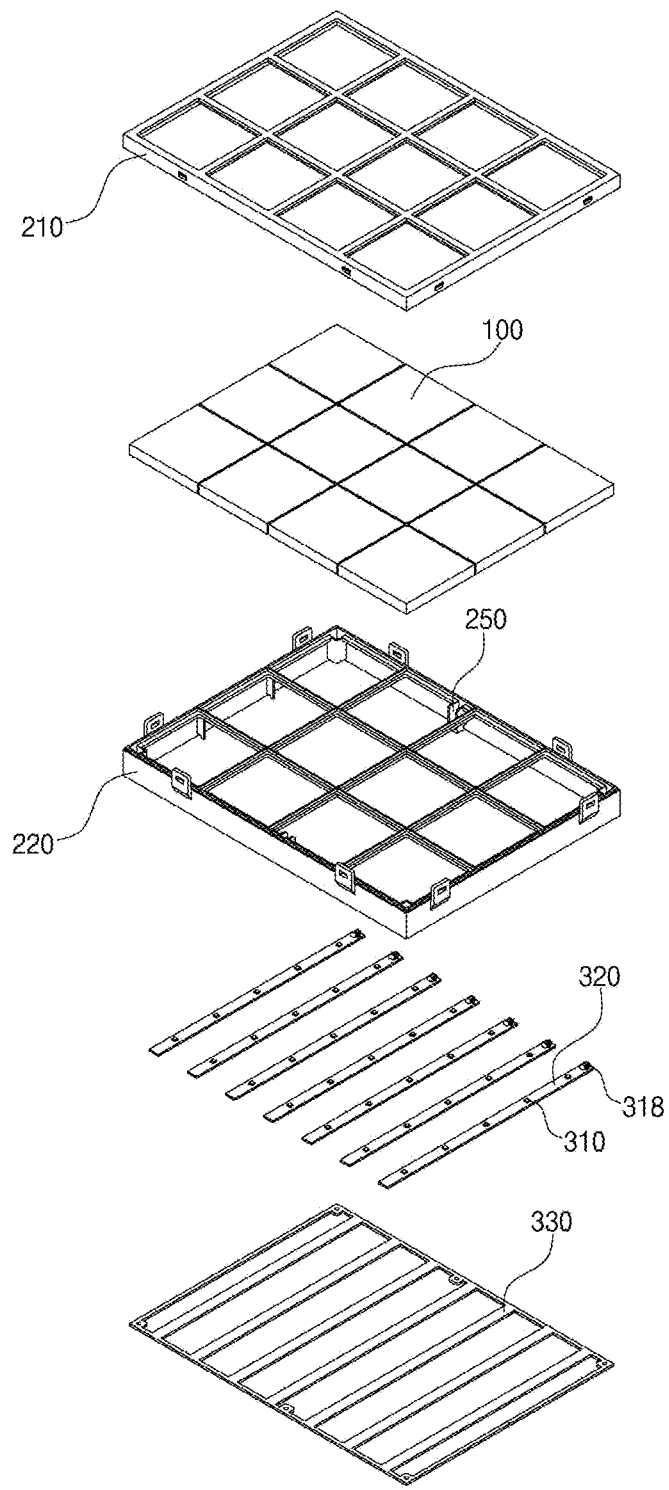
FIG. 8B is an exploded perspective view of the fluid treatment device of FIG. 8A.
Figure 8C:
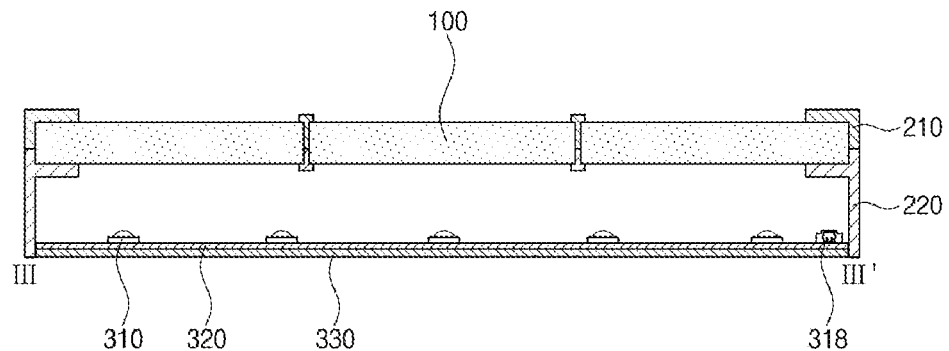
FIG. 8C is a sectional view of the fluid treatment device taken alone line III-III' of FIG. 8A.

FIG. 8A is a perspective view of a fluid treatment device according to yet another embodiment of the present invention and FIG. 8b is an exploded perspective view of the fluid treatment device of FIG. 8a. FIG. 8C is a sectional view of the fluid treatment device taken alone line III-III' of FIG. 8a.

Referring to FIG. 8A through 8C, the light source unit further includes an auxiliary member 330 coupled to a plurality of light source support members 320.

The auxiliary member 330 may be coupled to both the plurality of light source support members 320 and the second frame 220. Specifically, the auxiliary member 330 may be coupled to the second frame 220 via an auxiliary member coupling portion 250 provided to the second frame 220. Here, the auxiliary member coupling portion 250 may employ any suitable coupling method, without limitation.

When the auxiliary member 330 is coupled to the second frame 220 via the auxiliary member coupling portion 250, the coupling member coupling the second frame 220 to the light source support member 320 may be omitted. Specifically, the light source support member 320 may be disposed in the fluid treatment device by coupling the light source support member 320 to the auxiliary member 330 and coupling the auxiliary member 330 to the second frame 220.

Coupling between the light source support member 320 and the auxiliary member 330 may be established by any suitable coupling method without limitation. For example, coupling between the light source support member 320 and the auxiliary member 330 may be established via an adhesive. Alternatively, coupling between the light source support member 320 and the auxiliary member 330 may be achieved by screw-engagement, clip-engagement, or the like.

The light source support member 320 may be detachably coupled to the auxiliary member 330. Accordingly, when a problem occurs in a certain light source support member 320, it is possible to replace only the problematic light source support member 320.

Structural stability of the fluid treatment device can be improved by providing the plurality of light source support members 320 to the fluid treatment device via the auxiliary member 330. If the light source support members 320 are individually coupled to the second frame 220, the number of coupling members and protrusions for connecting the light source support members 320 to the second frame 220 increases exponentially with the increasing count of light source support members 320. An increasing number of protrusions of the second frame 220 may cause deterioration in rigidity of the second frame 220.

According to this embodiment, since the plurality of light source support members 320 is disposed on one auxiliary member 330, which in turn is coupled to the second frame 220, it is possible to prevent deterioration in rigidity of the second frame 220 even when the number of light source support members 320 is increased.

Thus, according to this embodiment, a large number of light source support members 320 and light emitting diodes 310 may be disposed in the fluid treatment device, thereby allowing ease of scale-up of the fluid treatment device.

In addition, when the auxiliary member 330 includes a metal, the auxiliary member 330 has high thermal conductivity and thus can dissipate heat generated from the light emitting diodes 310 and the light source support members 320.

Figure 9:
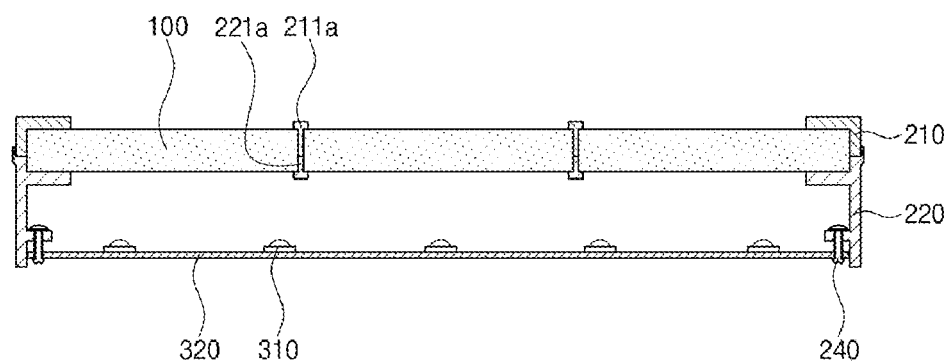
FIG. 9 is a sectional view of a fluid treatment device according to yet another embodiment.
Figure 10:
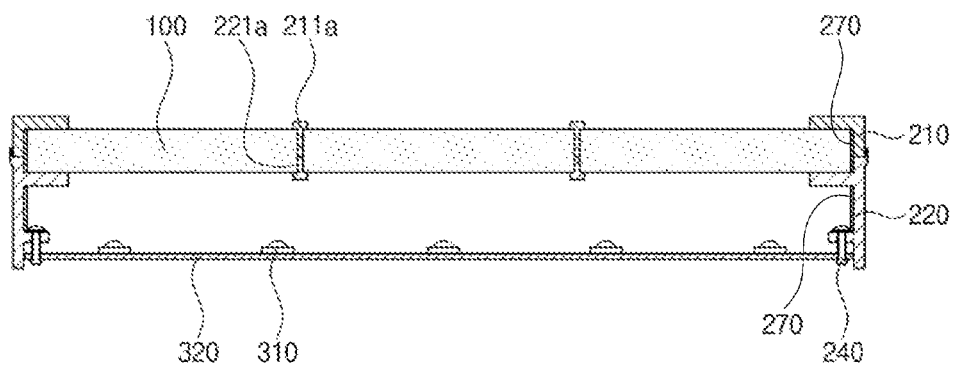
FIG. 10 is a sectional view of the fluid treatment device having a reflective member.

FIG. 9 and FIG. 10 are sectional views of a fluid treatment device according to yet other embodiments.

Referring FIG. 9, the second frame 220 is coupled to the light source support member 320 via a coupling member 240. Here, the coupling member 240 may couple the second frame 220 to the light source support member 320 by screw-engagement.

In addition, a user can adjust the distance between the light emitting diode 310 and the photocatalytic filter 100 by manipulating the coupling member 240.

Referring to FIG. 10, the fluid treatment device may further include a reflective member 270 formed on an inner wall of each of the first frame 210 and the second frame 220. The reflective member 270 reflects light emitted from the light emitting diode 310 toward the photocatalytic filter 100. Accordingly, irradiance delivered to the photocatalytic filter 100 can be increased, thereby allowing increase in photocatalytic activity.

Figure 11:
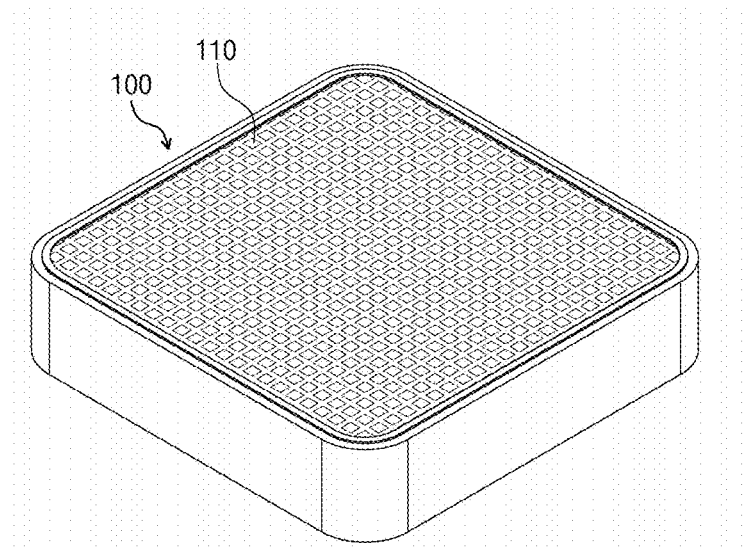
FIG. 11 is a perspective view of a photocatalytic filter according to one embodiment of the present invention.

FIG. 11 is a perspective view of a photocatalytic filter of according to another embodiment of the present disclosure.

In this embodiment, the photocatalytic filter 100 may have a cuboid shape having relatively wide upper and low surfaces.

The photocatalytic filter 100 may be configured to maximize a contact area between the photocatalytic filter 100 and air. For example, the photocatalytic filter 100 according to this embodiment may be provided in the form of a lattice having cells provided with a plurality of vertical openings 110 formed through the photocatalytic filter 100, respectively. However, it will be understood that other implementations are possible and the photocatalytic filter 100 may be provided in any other form that can increase the contact area between the photocatalytic filter 100 and air.

For example, the photocatalytic filter 100 may have a plurality of pores formed therein, instead of the vertical openings 110 formed therethrough. Here, the photocatalytic filter 100 may include a plurality of sintered beads coated with a photocatalytic material. The pores are disposed between the beads, thereby maximizing the contact area between the photocatalytic filter 100 and air.

The photocatalytic filter 100 includes a photocatalyst that can treat air by reacting with light emitted from the light source unit. Details of reaction of the photocatalyst are as described above.

The photocatalytic material may include at least one selected from the group of titanium dioxide ($TiO_2$), zirconia ($ZrO_2$), zinc oxide (ZnO), tungsten oxide ($WO_3$), and tin oxide ($SnO_2$). Since holes and electrons generated in the surface of the photocatalyst recombine at a very high rate, use of the photocatalyst in photochemical reaction can be limited. Accordingly, in embodiments of the present disclosure, a metal, such as Pt, Ni, Mn, Ag, W, Cr, Mo, or Zn, or an oxide thereof may be added to the photocatalyst to delay recombination of hole-electron pairs. Delay in recombination of hole-electron pairs can increase a possibility of contact with a target material to be oxidized and/or decomposed, thereby allowing increase in reactivity. Further, addition of the oxide allows adjustment of band gap energy of the photocatalyst, thereby improving performance of the photocatalyst. The photocatalytic reaction described above can allow sterilization, purification, and deodorization of air. Particularly, in regard to sterilization, the photocatalytic reaction provides sterilization or antibacterial activity by destroying enzymes in germ cells and enzymes affecting the respiratory system, and thus can prevent the growth of germs or fungi while decomposing toxins released thereby.

In some embodiments, titanium oxide ($TiO_2$) may be used as the photocatalyst. Upon receiving UV light, titanium oxide generates peroxide radicals that can decompose organic substances into water and carbon dioxide, which are harmless. In particular, titanium oxide nanoparticles can generate a large amount of peroxide radicals even under relatively weak UV illumination. Thus, titanium oxide has good ability to decompose organic substances, has high durability and stability even under environmental changes, and provides semi-permanent effects. In addition, a large amount of peroxide radicals generated by titanium oxide can remove or deodorize various substances, such as germs, in addition to organic substances.

In other embodiments, the photocatalyst is usable semi-permanently and provides semi-permanent effects so long as the photocatalyst is properly illuminated, since the photocatalyst just acts as a catalyst and the photocatalyst itself does not change.

A substrate or the beads, which are coated with the photocatalytic material, may include one selected from the group of alumina ($Al_2O_3$), silicon oxide ($SiO_2$), zirconia ($ZrO_2$), silicon nitride ($Si_3N_4$), silicon carbide (SiC), or a combinations thereof.

In addition, the photocatalytic filter 100 may further include an adsorbent for physical adsorption on the surface thereof. The adsorbent may be a porous material, such as zeolite. Since the adsorbent is used together with the photocatalytic material, pollutants adhered to the adsorbent can also be removed by the photocatalytic material. Accordingly, even when the photocatalytic filter 100 is used for a long time, the adsorbent can avoid significant degradation.

Figure 12:
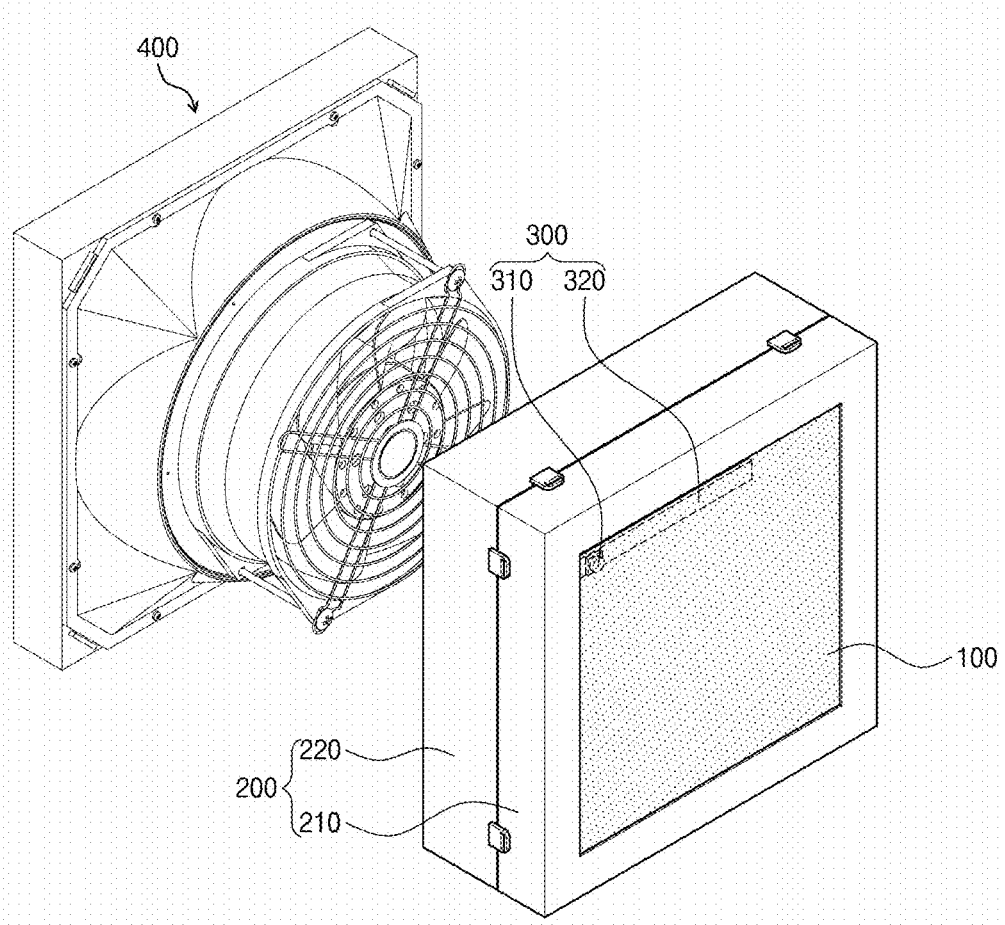
FIG. 12 is a perspective view of a fluid treatment device according to yet another embodiment of the present invention.

FIG. 12 is a perspective view of a fluid treatment device according to yet another embodiment.

Referring to FIG. 12, the fluid treatment device further includes a blower 400. The blower 400 may be advantageously used, particularly when a fluid to be treated by the fluid treatment device has a gas phase. The blower 400 serves to speed up the flow of the fluid, thereby increasing the volume of the fluid flowing into the fluid treatment device per unit time. As a result, the volume of the fluid treated by the fluid treatment device per unit time can be increased.

Although the blower 400 is shown as having one light source unit 300 and one photocatalytic filter 100 disposed in front the blower 400 as shown in FIG. 12, it will be understood that other implementations are possible. As shown in FIGS. 5A through FIG. 10, the fluid treatment device may include a plurality of light source units 300 and a plurality of photocatalytic filters 100. The light source units 300 and the photocatalytic filters 100 may be arranged one by one in front of the blower 400. In this way, it is possible to prevent reduction in degree of purification of the fluid by the fluid treatment device even when the volume of the fluid flowing into the fluid treatment device per unit time is increased.

Figure 13:
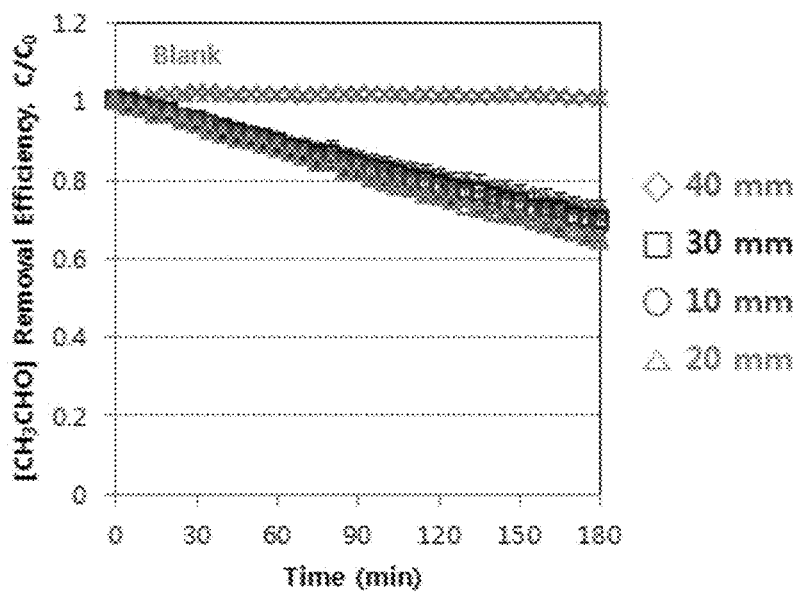
FIG. 13 is a graph showing decontamination performance of a fluid treatment device depending upon the distance between a light emitting diode and a photocatalytic filter with respect to a time and acetaldehyde removal efficiency.
Figure 14:
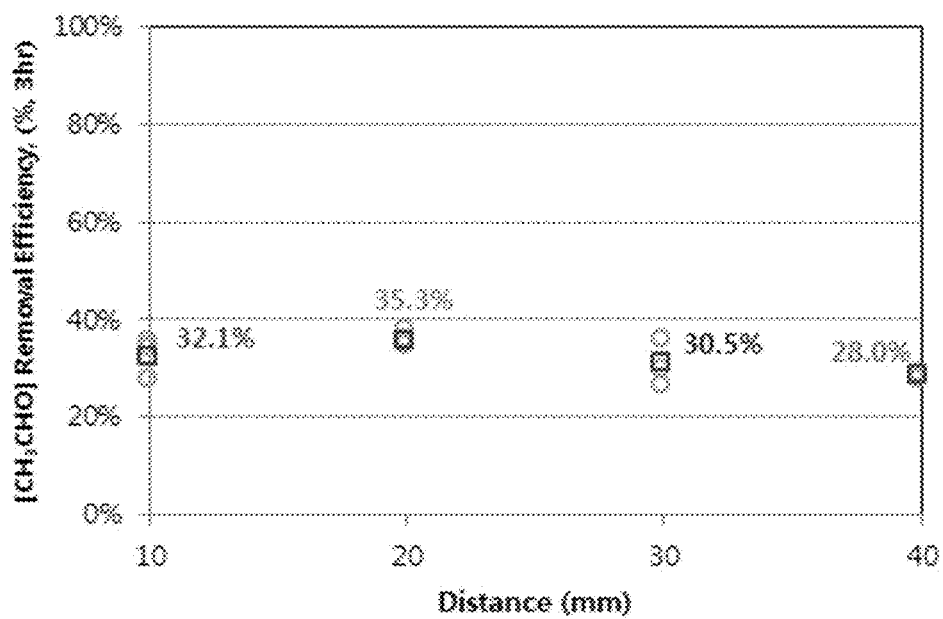
FIG. 14 is another graph showing decontamination performance of a fluid treatment device depending upon the distance between the light emitting diode and the photocatalytic filter with respect to a distance and acetaldehyde removal efficiency.

FIG. 13 and FIG. 14 are graphs showing decontamination performance of a fluid treatment device according to the embodiments described above depending upon a distance between a light emitting diode and a photocatalytic filter.

The experimental data shown in FIG. 13 and FIG. 14 was obtained using one photocatalytic filter and one light emitting diode according to the embodiments described above. Specifically, the photocatalytic filter had a size of 33 mm×33 mm×10 mm (length×width×thickness) and the light emitting diode emitted light having a wavelength of about 365 nm at a current of 300 mA. A blower was placed at the rear of the light emitting diode to force a fluid toward the photocatalytic filter. Here, the blower was set to force the fluid toward the photocatalytic filter at a rate of 0.12 $m^3$/min at a driving voltage of 12 V.

FIG. 13 and FIG. 14 show data on how much acetaldehyde gas (10 ppm) could be purified for 180 minutes when the distance between the light emitting diode and the photocatalytic filter was set to 10 mm, 20 mm, 30 mm, and 40 mm.

Experimental results show that about 32.1% of acetaldehyde could be removed in about 3 hours when the distance between the light emitting diode and the photocatalytic filter was set to 10 mm and about 35.3% of acetaldehyde could be removed in about 3 hours when the distance between the light emitting diode and the photocatalytic filter was set to 20 mm. In addition, about 30.5% of acetaldehyde could be removed in about 3 hours when the distance between the light emitting diode and the photocatalytic filter was set to 30 mm and about 28.0% of acetaldehyde could be removed for about 3 hours when the distance between the light emitting diode and the photocatalytic filter was set to 40 mm.

These experimental results are considered to be due to the fact that sufficient irradiance to activate the photocatalytic filter can be delivered over an maximized illumination area of the photocatalytic filter when the distance between the light emitting diode and the photocatalytic filter is 20 mm. Irradiance and illumination region depending upon the distance between the light emitting diode and the photocatalytic filter are shown in Table 1.

TABLE 1

| Distance | Diameter of illumination region | Area of illumination region | Irradiance |
| --- | --- | --- | --- |
| 10 mm | 34.64 mm | 9.42 cm$^2$ | 21.72 mW/cm$^2$ |
| 20 mm | 69.28 mm | 37.68 cm$^2$ | 20.23 mW/cm$^2$ |
| 30 mm | 103.92 mm | 84.78 cm$^2$ | 15.52 mW/cm$^2$ |
| 40 mm | 138.56 mm | 150.71 cm$^2$ | 11.81 mW/cm$^2$ |

As shown in Table 1, when the distance between the light emitting diode and the photocatalytic filter was set to about 20 mm, sufficient irradiance (about 20.23 mW/cm$^2$) to activate the photocatalytic filter can be secured. When the distance between the light emitting diode and the photocatalytic filter was set to about 10 mm, the irradiance delivered to the photocatalytic filter was greater than when the distance between the light emitting diode and the photocatalytic filter was set to about 20 mm, but the illumination region decreased to ¼ of that when the distance between the light emitting diode and the photocatalytic filter was set to about 20 mm. Therefore, sufficient irradiance to activate the photocatalytic filter can be delivered over a maximized illumination area of the photocatalytic filter when the distance between the light emitting diode and the photocatalytic filter is about 20 mm, as demonstrated in FIGS. 13 and 14 based on differences in aldehyde removal efficiency.

What is claimed is:

1. A fluid treatment device, comprising:
   at least one photocatalytic filter including a surface coated with a photocatalyst and activated by illumination of light and for deodorizing and sterilizing a fluid;
   a frame holding the at least one photocatalytic filter; and
   a light source unit coupled to the frame, the light source unit comprising:
      at least one light emitting diode to emit light toward the at least one photocatalytic filter; and
      at least one light source support member comprising an upper surface on which the at least one light emitting diode is disposed and a lower surface opposite to the upper surface and having a reflective portion on the upper surface to reflect the light from the at least one light emitting diode toward the at least one photocatalytic filter;
   wherein the at least one light source support member and the at least one photocatalytic filter are coupled to the frame such that the at least one photocatalytic filter is spaced apart from the at least one light emitting diode by a predetermined distance and maintains the predetermined distance;
   wherein a ratio D/L of a diameter D of an illumination region over the at least one photocatalytic filter by the at least one light emitting diode to a first distance L between the at least one photocatalytic filter and the at least one light emitting diode is within a preset range;
   wherein:
      the first distance L and a position of the at least one light emitting diode on the upper surface are adjustable to irradiate the light from the at least one light emitting diode such that the diameter D of the illumination region is maximized and light from one light emitting diode, or light from two or more light emitting diodes, taken together, reaches a substantially entire area of the at least one photocatalytic filter; and
      irradiance of the light over the illumination region does not exceed 21.72 mW/cm$^2$, regardless of different values of the first distance.

2. The fluid treatment device according to claim 1, wherein the at least one photocatalytic filter comprises a plurality of photocatalytic filters.

3. The fluid treatment device according to claim 2, wherein the plurality of photocatalytic filters is placed in a same plane.

4. The fluid treatment device according to claim 2, wherein the frame comprises one or more ribs disposed between the plurality of photocatalytic filters.

5. The fluid treatment device according to claim 4, wherein a separation distance between neighboring photocatalytic filters correspond to a width of a rib interposed between the neighboring photocatalytic filters.

6. The fluid treatment device according to claim 1, wherein the at least one light emitting diode has an angle of beam that spreads of 120 degrees or less, the beam reaching the at least one photocatalytic filter from the at least one light emitting diode within the predetermined distance.

7. The fluid treatment device according to claim 1, wherein the ratio D/L between the at least one photocatalytic filter and the at least one light emitting diode ranges from 3.46 to 3.50.

8. The fluid treatment device according to claim 1, wherein the frame comprises a first frame and a second frame, and the at least one photocatalytic filter is disposed between the first frame and the second frame.

9. The fluid treatment device according to claim 8, wherein the at least one photocatalytic filter comprises a plurality of photocatalytic filters, and the first frame and the second frame comprise a first rib and a second rib, respectively, the first rib and the second rib each being disposed between the plurality of photocatalytic filters.

10. The fluid treatment device according to claim 1, wherein the at least one light source support member comprises a plurality of light source support members and the light source unit further comprises an auxiliary member coupled to the plurality of light source support members.

11. The fluid treatment device according to claim 10, wherein the auxiliary member comprises a metal and dissipates heat generated from the at least one light emitting diode and the plurality of light source support members.

12. The fluid treatment device according to claim 1, wherein the light source unit comprises a plurality of light emitting diodes disposed on the at least one light source support member.

13. The fluid treatment device according to claim 1, wherein the frame further comprises a coupling member connecting the frame to the at least one light source support member, the coupling member further comprising a detachable engagement structure and being used to adjust a second distance between the frame and the at least one light source support member.

14. The fluid treatment device according to claim 1, wherein the at least one light emitting diode comprises a plurality of light emitting diodes separated from one another with the at least one photocatalytic filter in between.

15. The fluid treatment device according to claim 1, wherein the at least one photocatalytic filter comprises:
    a plurality of sintered beads having a surface coated with a photocatalytic material; and
    pores disposed between the beads.

16. The fluid treatment device according to claim 15, wherein the beads comprise alumina ($Al_2O_3$), silicon oxide ($SiO^2$), zirconia ($ZrO_2$), silicon nitride ($Si_3N_4$), or silicon carbide (SiC), or a combinations thereof.

17. The fluid treatment device according to claim 15, wherein the photocatalytic material comprises titanium dioxide ($TiO_2$), zirconia ($ZrO_2$), zinc oxide (ZnO), tungsten oxide ($WO_3$), or tin oxide ($SnO_2$).

18. The fluid treatment device according to claim 1, wherein the at least one light emitting diode emits light having a wavelength in a UV wavelength band.

19. The fluid treatment device according to claim 1, further comprising:
    a blower forcing a fluid toward the at least one photocatalytic filter.

20. The fluid treatment device according to claim 1, wherein the at least one photocatalytic filter includes a plurality of photocatalytic filters arranged side by side in a first direction,
    wherein the light source unit comprises an upper light source unit and a lower light source unit, each light source unit including a plurality of light emitting diodes spaced apart from each other in the first direction,
    wherein the plurality of photocatalytic filters is disposed between the upper light source unit and the lower light source unit in a second direction perpendicular to the first direction, and
    wherein each light emitting diode of the upper light source unit is spaced apart from each light emitting diode of the lower light source unit in the first direction such that the plurality of light emitting diodes of the upper light source unit are not aligned with the plurality of light emitting diodes of the lower light source unit in the second direction.

* * * * *